(12) United States Patent
Keilhack et al.

(10) Patent No.: US 10,898,490 B2
(45) Date of Patent: *Jan. 26, 2021

(54) METHOD FOR TREATING CANCER

(71) Applicant: Epizyme, Inc., Cambridge, MA (US)

(72) Inventors: Heike Keilhack, Belmont, MA (US); Sarah K. Knutson, Lincoln, MA (US)

(73) Assignee: Epizyme, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/660,185

(22) Filed: Oct. 22, 2019

(65) Prior Publication Data

US 2020/0155561 A1 May 21, 2020

Related U.S. Application Data

(63) Continuation of application No. 15/754,684, filed as application No. PCT/US2016/048401 on Aug. 24, 2016, now Pat. No. 10,493,076.

(60) Provisional application No. 62/209,304, filed on Aug. 24, 2015.

(51) Int. Cl.
| | |
|---|---|
| *A61K 31/5377* | (2006.01) |
| *A61K 31/4412* | (2006.01) |
| *A61K 31/4545* | (2006.01) |
| *A61P 35/00* | (2006.01) |
| *A61K 9/00* | (2006.01) |

(52) U.S. Cl.
CPC ........ *A61K 31/5377* (2013.01); *A61K 9/0053* (2013.01); *A61K 31/4412* (2013.01); *A61K 31/4545* (2013.01); *A61P 35/00* (2018.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,455,044 A | 10/1995 | Kim et al. |
| 8,410,088 B2 | 4/2013 | Kuntz et al. |
| 8,536,179 B2 | 9/2013 | Miller et al. |
| 8,598,167 B1 | 12/2013 | Kuntz et al. |
| 8,691,507 B2 | 4/2014 | Copeland et al. |
| 8,765,732 B2 | 7/2014 | Kuntz et al. |
| 8,895,245 B2 | 11/2014 | Copeland et al. |
| 8,962,620 B2 | 2/2015 | Kuntz et al. |
| 9,006,242 B2 | 4/2015 | Kuntz et al. |
| 9,089,575 B2 | 7/2015 | Kuntz et al. |
| 9,090,562 B2 | 7/2015 | Kuntz et al. |
| 9,175,331 B2 | 11/2015 | Kuntz et al. |
| 9,206,157 B2 | 12/2015 | Kuntz et al. |
| 9,334,527 B2 | 5/2016 | Kuntz et al. |
| 9,469,646 B2 | 10/2016 | Albrecht et al. |
| 9,522,152 B2 | 12/2016 | Kuntz et al. |
| 9,549,931 B2 | 1/2017 | Kuntz et al. |
| 9,688,665 B2 | 6/2017 | Knutson et al. |
| 9,855,275 B2 | 1/2018 | Kuntz et al. |
| 9,889,138 B2 | 2/2018 | Keilhack |
| 10,155,002 B2 | 12/2018 | Kuntz et al. |
| 10,420,775 B2 | 9/2019 | Kuntz et al. |
| 10,463,671 B2 | 11/2019 | Keilhack et al. |
| 10,493,076 B2 * | 12/2019 | Keilhack ................ A61P 35/00 |
| 2003/0175736 A1 | 9/2003 | Chinnaiyan et al. |
| 2005/0107290 A1 | 5/2005 | Ito et al. |
| 2009/0012031 A1 | 1/2009 | Chinnaiyan et al. |
| 2011/0064664 A1 | 3/2011 | Lopez-Berestein et al. |
| 2012/0071418 A1 | 3/2012 | Copeland et al. |
| 2012/0114670 A1 | 5/2012 | Land et al. |
| 2012/0264734 A1 | 10/2012 | Kuntz et al. |
| 2013/0040906 A1 | 2/2013 | Kuntz et al. |
| 2013/0053383 A1 | 2/2013 | Duquenne et al. |
| 2014/0296248 A1 | 10/2014 | Bernards et al. |
| 2015/0065483 A1 | 3/2015 | Kuntz et al. |
| 2015/0065503 A1 | 3/2015 | Kuntz et al. |
| 2015/0352119 A1 | 12/2015 | Kuntz et al. |
| 2015/0353494 A1 | 12/2015 | Kuntz et al. |
| 2015/0368229 A1 | 12/2015 | Albrecht et al. |
| 2016/0022693 A1 | 1/2016 | Kuntz et al. |
| 2016/0228447 A1 | 8/2016 | Keilhack et al. |
| 2016/0326596 A1 | 11/2016 | Levine et al. |
| 2017/0305889 A1 | 10/2017 | Knutson et al. |
| 2017/0305890 A1 | 10/2017 | Knutson et al. |
| 2018/0296563 A1 | 10/2018 | Keilhack |
| 2019/0038633 A1 | 2/2019 | Smith et al. |
| 2019/0070188 A1 | 3/2019 | Keilhack et al. |
| 2019/0083504 A1 | 3/2019 | Keilhack et al. |
| 2019/0100514 A1 | 4/2019 | Knutson et al. |
| 2019/0240230 A1 | 8/2019 | Keilhack et al. |
| 2019/0255060 A1 | 8/2019 | Keilhack et al. |
| 2019/0315725 A1 | 10/2019 | Keilhack et al. |
| 2019/0350929 A1 | 11/2019 | Ribich |
| 2020/0138825 A1 | 5/2020 | Keilhack et al. |
| 2020/0262823 A1 | 8/2020 | Knutson et al. |
| 2020/0268765 A1 | 8/2020 | Keilhack et al. |

FOREIGN PATENT DOCUMENTS

| | | |
|---|---|---|
| WO | WO 2009/006577 A2 | 1/2009 |
| WO | WO 2011/103016 A2 | 8/2011 |
| WO | WO 2011/140324 A1 | 11/2011 |
| WO | WO 2012/034132 A2 | 3/2012 |
| WO | WO 2012/068589 A2 | 5/2012 |
| WO | WO 2012/071096 A2 | 5/2012 |
| WO | WO 2012/075080 A1 | 6/2012 |
| WO | WO 2012/118812 A2 | 9/2012 |
| WO | WO 2012/138783 A2 | 10/2012 |
| WO | WO 2012/142504 A1 | 10/2012 |
| WO | WO 2012/142513 A1 | 10/2012 |
| WO | WO 2013/039988 A1 | 3/2013 |
| WO | WO 2013/049770 A2 | 4/2013 |

(Continued)

OTHER PUBLICATIONS

U.S. Appl. No. 15/987,000, filed May 23, 2018, Knutson et al.

(Continued)

*Primary Examiner* — Brian J Davis
(74) *Attorney, Agent, or Firm* — Cooley LLP; Heidi A. Erlacher; Christine C. Pemberton

(57) ABSTRACT

The present disclosure relates to pharmaceutical compositions comprising inhibitor(s) of human histone methyltransferase EZH2, and methods of cancer therapy using the EZH2 inhibitor(s).

11 Claims, No Drawings

(56) References Cited

FOREIGN PATENT DOCUMENTS

| | | |
|---|---|---|
| WO | WO 2013/059944 A1 | 5/2013 |
| WO | WO 2013/120104 A2 | 8/2013 |
| WO | WO 2013/138361 A1 | 9/2013 |
| WO | WO 2013/140148 A1 | 9/2013 |
| WO | WO 2013/155317 A1 | 10/2013 |
| WO | WO 2013/155464 A1 | 10/2013 |
| WO | WO 2013/173441 A1 | 11/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO 2014/124418 A1 | 8/2014 |
| WO | WO 2014/144747 A1 | 9/2014 |
| WO | WO 2014/172044 A1 | 10/2014 |
| WO | WO 2014/176047 A1 | 10/2014 |
| WO | WO 2014/177982 A1 | 11/2014 |
| WO | WO 2014/195919 A1 | 12/2014 |
| WO | WO 2015/004618 A1 | 1/2015 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/103431 A1 | 7/2015 |
| WO | WO 2015/128837 A1 | 9/2015 |
| WO | WO 2015/132765 A1 | 9/2015 |
| WO | WO 2015/143012 A1 | 9/2015 |
| WO | WO 2015/193768 A1 | 12/2015 |
| WO | WO 2015/195848 A1 | 12/2015 |
| WO | WO 2015/200650 A9 | 12/2015 |
| WO | WO 2016/061507 A1 | 4/2016 |
| WO | WO 2016/081523 A1 | 5/2016 |
| WO | WO 2016/172199 A1 | 10/2016 |
| WO | WO 2016/201328 A1 | 12/2016 |
| WO | WO 2017/053930 A2 | 3/2017 |
| WO | WO 2017/062495 A2 | 4/2017 |
| WO | WO 2017/079757 A1 | 5/2017 |
| WO | WO 2017/100362 A2 | 6/2017 |
| WO | WO 2017/132518 A1 | 8/2017 |
| WO | WO 2017/139404 A1 | 8/2017 |
| WO | WO 2018/144798 A1 | 8/2018 |

OTHER PUBLICATIONS

"Myoepithelial carcinoma" [online]. Genetic and Rare Diseases Information Center (GARD). Retrieved from: https://rarediseases.info.nih.gov/diseases/10558/myoepithelial-carcinoma; downloaded Mar. 20, 2020, 4 pages.

Alarcon-Vargas, D. et al. (Feb. 2, 2006) "Targeting cyclin D1, a downstream effector of INI1/hSNF5, in rhabdoid tumors" *Oncogene*, 25(5):722-734 (Abstract only, retrieved from: https://www.ncbi.rilm.nih.gov/pubmed/16302003, 2 pages).

Alimova, I. et al. (2012) "Targeting the enhancer of zeste homologue 2 in medulloblastoma" *Intl J Cancer*, 131:1800-1809 [online]. Retrieved from the Internet: https://onlinelibrary.wiley.com/doi/full/10.1002/ijc.27455; 15 pages.

Alimova, I. et al. (2013) "Inhibition of EZH2 Suppresses Self-Renewal and Induces Radiation Sensitivity in Atypical Rhabdoid Teratoid Tumor Cells" *Neuro-Oncology*, 15(2):149-160.

Belikov, V.G. *Pharmaceutical Chemistry*. High School, 1993; pp. 43-47. Russian with English translation, 14 pages.

Betz, B.L. et al. (2002) "Re-expression of hSNF5/INI1/BAF47 in pediatric tumor cells leads to $G_1$ arrest associated with induction of p16ink4a and activation of RB" *Oncogene*, 21:5193-5203.

Campbell, J.E. et al. (Mar. 4, 2015) "EPZ011989, A Potent, Orally-Available EZH2 Inhibitor with Robust in Vivo Activity" *ACS Med Chem Lett*, 6:491-495.

Cascio, M.J. et al. (2010) "Epithelioid sarcoma expresses epidermal growth factor receptor but gene amplification and kinase domain mutations are rare" *Modern Pathology*, 23:574-580.

Chang et al. (2012) "The role of EZH2 in tumour progression" *Br J Cancer*, 106:243-247.

Chan-Penebre, E. et al. (2017) "Selective Killing of SMARCA2- and SMARCA4-deficient Small Cell Carcinoma of the Ovary, Hypercalcemic Type Cells by Inhibition of EZH2: In Vitro and In Vivo Preclinical Models" *Mol Cancer Ther*, 16(5):850-860.

Chase, A. and N.C. Cross (2011) "Aberrations of EZH2 in cancer" *Clin Cancer Res*, 17(9):2613-2618.

Chen, H. et al. (1996) "Cloning of a Human Homolog of the *Drosophila* Enhancer of zeste Gene (EZH2) That Maps to Chromosome 21q22.2" *Genomics*, 38:30-37.

Cheng, S.-W. G. et al. (May 1999) "c-MYC interacts with INI1/hSNF5 and requires the SWI/SNF complex for transactivation function" *Nat Genet*, 22:102-105.

Ciarapica, R. et al. (2011) "Enhancer of zeste homolog 2 (EZH2) in pediatric soft tissue sarcomas: first implications" *BMC Medicine*, 9:63, 9 pages.

Copeland, R.A. (2013) "Molecular pathways: protein methyltransferases in cancer" *Clin Cancer Res*, 19(23):6344-6350.

Desouza, R-M. et al. (Jul. 22, 2014) "Pediatric medulloblastoma—update on molecular classification driving targeted therapies" *Frontiers in Oncology*, vol. 4, Article 176, 8 pages.

Dhanak, D. and P. Jackson (2014) "Development and classes of epigenetic drugs for cancer" *Biochem Biophys Res Commun*, 455:58-69.

Fillmore et al. (2015) "EZH2 inhibition sensitizes BRG1 and EGFR mutant lung tumors to TopoII inhibitors" *Nature*, 520(7546):239-242. HHS Public Access Author Manuscript; available in PMC Oct. 9, 2015, 21 pages.

Fiskus et al. (2009) "Combined epigenetic therapy with the histone methyltransferase EZH2 inhibitor 3-deazaneplanocin A and the histone deacetylase inhibitor panobinostat against human AML cells" *Blood*, 114(13):2733-2743.

Foulkes, W.D. et al. (2014) "No small surprise—small cell carcinoma of the ovary, hypercalcaemic type, is a malignant rhabdoid tumour" *J Pathol*, 233:209-214.

Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol*, 20:1329-1339.

Genentech, Inc. (May 6, 2016) TECENTRIQ™: *Highlights of Prescribing Information* [online]. Retrieved from: https://www.accessdata.fda.gov/drugsaffda_docs/label/2016/761034s000lbl.pdf; retrieved on Nov. 12, 2019, 17 pages.

Gounder, M. et al. "Phase 2 Multicenter Study of the EZH2 Inhibitor Tazemetostat in Adults with INI1 Negative Epithelioid Sarcoma (ES) (NCT02601950)" Poster 381 presented at ASCO, Chicago, IL, on Jun. 4, 2017, 1 page.

Helming, K.C. et al. (Sep. 8, 2014) "Vulnerabilities of mutant SWI/SNF complexes in cancer" *Cancer Cell*, 26:309-317.

Hollmann, T.J. et al. (Oct. 2011) "INI1-Deficient Tumors: Diagnostic Features and Molecular Genetics" *Am J Surg Pathol*, 35(10):e47-e63.

Hornick, J.L. et al. (2009) "Loss of INI1 expression is characteristic of both conventional and proximal-type epithelioid sarcoma" *Am J Surg Pathol*, 33(4):542-550.

Italiano, A. et al. (Sep. 2015) "A phase 1 study of EPZ-6438 (E7438), an Enhancer of Zeste-Homolog 2 (EZH2) inhibitor: Preliminary activity in INI1-negative tumors" *Eur J Cancer*, 51(Suppl 3): S54-S55, Abstract.

Jagani, Z. et al. (2010) "Loss of the tumor suppressor Snf5 leads to aberrant activation of the Hedgehog-Gli pathway" *Nat Med*, 16:1429-1433. NIH Public Access Author Manuscript; available in PMC Dec. 11, 2013; 12 pages.

Januario, T. et al. (Nov. 14, 2017) "PRC2-mediated repression of SMARCA2 predicts EZH2 inhibitor activity in SWI/SNF mutant tumors" *PNAS*, 114(46):12249-12254.

Jelinic, P. et al. (2014) "Recurrent SHARCA4 mutations in small cell carcinoma of the ovary" *Nat Genet*, 46:424-426. HHS Public Access Author Manuscript, retrieved from the Internet: https://www.ncbi.nlm.nih.gov/pmc/articles/PMC5699446/pdf/nihms920036.pdf, 10 pages.

Jo, V.Y. et al. (May 2015) "Epthelioid Malignant Peripheral Nerve Sheath Tumor" *Am J Surg Pathol*, 39(5):673-682.

(56) References Cited

OTHER PUBLICATIONS

Kadoch, C. et al. (2013) "Reversible Disruption of mSW1/SNF (BAF) Complexes by the SS18-SSX Oncogenic Fusion in Synovial Sarcoma" *Cell*, 153:71-85.

Kadoch, C. et al. (2016) "PRC2 and SWI/SNF Chromatin Remodeling Complexes in Health and Disease" *Biochemistry*, 55(11):1600-1614.

Karnezis, A.N. et al. (2016) "Dual loss of the SWI/SNF complex ATPases SMARCA4/BRG1 and SMARCA2/BRM is highly sensitive and specific for small cell carcinoma of the ovary, hypercalcaemic type" *J Pathol*, 238:389-400.

Kim, K.H. et al. (Sep. 2014) "Mechanisms by which SMARCB1 loss drives rhabdoid tumor growth" *Cancer Genet*, 207:365-372. NIH Public Access Author Manuscript; available in PMC Sep. 1, 2015; 15 pages.

Kleer, C.G. et al. (Sep. 30, 2003) "EZH2 is a marker of aggressive breast cancer and promotes neoplastic transformation of breast epithelial cells" *Proc Natl Acad Sci USA*, 100(20):11606-11611.

Knutson, S.K. et al. (2012) "A Selective Inhibitor of EZH2 Blocks H3K27 Methylation and Kills Mutant Lymphoma Cells" *Nat Chem Biol*, 8:890-896.

Knutson, S.K. et al. (2013) "Durable tumor regression in genetically altered malignant rhabdoid tumors by inhibition of methyltransferase EZH2" *Proc Natl Acad Sci USA*, 110(19):7922-7927.

Knutson, S.K. et al. (Apr. 2014) "Selective inhibition of EZH2 by EPZ-6438 leads to potent antitumor activity in EZH2-mutant non-Hodgkin lymphoma" *Mol Cancer Ther*, 13(4):842-854.

Knutson, S.K. et al. (Dec. 10, 2014) "Synergistic antitumor activity of EZH2 inhibitors and glucocorticoid receptor agonists in models of germinal center non-Hodgkin lymphomas" *PLoS One*, 9(12):e111840, 22 pages.

Kupryjanczyk, J. et al. (2013) "Ovarian small cell carcinoma of hypercalcemic type—evidence of germline origin and SMARCA4 gene inactivation. A pilot study" *Pol J Pathol*, 64:238-246.

Kurmasheva, R.T. et al. (Mar. 2017) "Initial testing (stage 1) of tazemetostat (EPZ-6438), a novel EZH2 inhibitor, by the Pediatric Preclinical Testing Program" *Pediatric Blood & Cancer*, 64(3):DOI: 10.1002/pbc.26218. HHS Public Access Author Manuscript, available in PMC Mar. 1, 2018, 17 pages.

Kuwahara, Y. et al. (Mar. 1, 2010) "Reexpression of hSNF5 in malignant rhabdoid tumor cell lines C156causes cell cycle arrest through a p21CIP1/WAF1-dependent mechanism" *Cancer Res*, 70(5):1854-1865. NIH Public Access Author Manuscript, available in PMC Mar. 1, 2011, 18 pages.

Li, Y. et al. (Mar. 4, 2003) "Selective killing of cancer cells by β-lapachone: Direct checkpoint activation as a strategy against cancer" *PNAS*, 100(5):2674-2678.

Margueron, R. and D. Reinberg (2011) "The Polycomb complex PRC2 and its mark in life" *Nature*, 469(7330):343-349.

Matsubara, D. et al. (2013) "Lung cancer with loss of BRG1/BRM, shows epithelial mesenchymal transition phenotype and distinct histologic and genetic features" *Cancer Sci*, 104(2):266-273.

Mccabe, M.T. et al. (2012) "EZH2 inhibition as a therapeutic strategy for lymphoma with EZH2-activating mutations" *Nature*, 492:108-112.

Mckenna, E.S. et al. (2012) "Epigenetic inactivation of the tumor suppressor BIN1 drives proliferation of SNF5-deficient tumors" *Cell Cycle*, 11(10):1956-1965.

Medjkane, S. et al. (May 15, 2004) "The Tumor Suppressor hSNF5/INI1 Modulates Cell Growth and Actin Cytoskeleton Organization" *Cancer Research*, 64:3406-3413.

Oike, T. et al. (Sep. 1, 2013) "A Synthetic Lethality-Based Strategy to Treat Cancers Harboring a Genetic Deficiency in the Chromatin Remodeling Factor BRG1" *Cancer Res*, 73(17):5508-5518.

Oike, T. et al. (Feb. 11, 2014) "Chromatin-regulating proteins as targets for cancer therapy" *J Radiation Res*, 55:613-628.

Oruetxebarria, I. et al. (Jan. 30, 2004) "p16$^{INK4a}$ Is Required for hSNF5 Chromatin Remodeler-induced Cellular Senescence in Malignant Rhabdoid Tumor Cells" *J Biol Chem*, 279(5):3807-3816.

Qi, W. et al. (2012) "Selective inhibition of Ezh2 by a small molecule inhibitor blocks tumor cells proliferation" *Proc Natl Acad Sci USA*, 109(52):21360-21365.

Rabinovich, A. et al. (2015) "Primary rhabdoid tumor of the ovary: When large cells become small cells" *Gynecologic Oncology Reports*, 12:64-66.

Ramli, R. et al. (Jun. 2018) "An Analysis of Putative Cells of Origin for Malignant Rhabdoid Tumours (MRT): A Frontier for Development of MRT Cancer Modelling and Identification of Potential Therapeutic Targets" *Neuro-Oncol*, 20(Suppl 2): i33, ATRT-26; 1 page.

Ramos, P. et al. (2014) "Small cell carcinoma of the ovary, hypercalcemic type, displays frequent inactivating germline and somatic mutations in SMARCA4" *Nat Genet*, 46: 427-429. NIH Public Access Author Manuscript, retrieved from the Internet: https://www.ncbi.nlm.nih.gov/pmc/articles/PMC4332808/, 9 pages.

Reisman, D. et al. (Apr. 9, 2009) "The SWI/SNF complex and cancer" *Oncogene*, 28(14):1653-1668.

Reisman, D.N. et al. (2003) "Loss of BRG1/BRM in human lung cancer cell lines and primary lung cancers: correlation with poor prognosis" *Cancer Res*, 63(3):560-566.

Shain, A.H. et al. (Jan. 2013) "The spectrum of SWI/SNF mutations, ubiquitous in human cancers" *PLOS One*, 8(1):e55119, 11 pages.

Smith, M.E. et al. (Jan. 15, 2008) "Rhabdoid tumor growth is inhibited by flavopiridol" *Clin Cancer Res*, 14(2):523-532.

Srendi, S.T. et al. (Mar. 2010) "Upregulation of mir-221 and mir-222 in atypical teratoid/rhabdoid tumors: potential therapeutic targets" *Childs Nerv Sys*, 26(3):279-283. (Abstract only, retrieved from: https://www.ncbi.nlm.nih.gov/pubmed/20012062, 2 pages).

Sugimoto, T. et al. (1999) "Malignant Rhabdoid-Tumor Cell Line Showing Neural and Smooth-Muscle-Cell Phenotypes" Int J Cancer, 82:678-686, doi.org/10.1002/(SICI)1097-0215(Aug. 27, 1999)82:5<678::AID-IJC10>3.0.CO;2-K [online]. Retrieved from: https://onlinelibrary.wiley.com/doi/full/10.1002/%28SICI%291097-0215%2819990827%2982%3A5%3C678%3A%3AAID-IJC10%3E3.0.CO%3B2-K?sid=nlm%3Apubmed; 27 printed pages.

Thomas, A. et al. (Sep. 2015) "Refining the treatment of NSCLC according to histological and molecular subtypes" *Nat Rev Clin Oncol*, 12(9):511-526.

Tuma, R.S. et al. (2010) "Targeted Epigenetic Therapies: The Next Frontier?" *Journal of the National Cancer Institute*, 102(24):1824-1825.

UniProtKB/Swiss-Prot Accession No. Q15910 (Mar. 21, 2012) "EZH2 Human" [online]. Retrieved from the Internet: http://www.uniprot.org/uniprot/Q15910.txt?version=113; retrieved on Jul. 23, 2012, 10 pages.

Varambally, S. et al. (2002) "The Polycomb Group Protein EZH2 Is Involved in Progression of Prostate Cancer" *Nature*, 419:624-629.

Verbraecken, J. et al. (2006) "Body surface area in normal-weight, overweight, and obese adults. A comparison study" *Metabolism Clinical and Experimental*, 55:515-524.

Wilson, B.G. and C.W.M. Roberts (2011) "SWI/SNF nucleosome remodellers and cancer" *Nat Rev Cancer*, 11:481-492.

Wilson, B.G. et al. (Oct. 2010) "Epigenetic Antagonism between Polycomb and SWI/SNF Complexes during Oncogenic Transformation" *Cancer Cell*, 18(4):316-328.

Witkowski, L. et al. (May 2014) "Germline and somatic SMARCA4 mutations characterize small cell carcinoma of the ovary, hypercalcemic type" *Nat Genet*, 46(5):438-443, including "Methods", 2 pages.

Zhang, P. et al. (Mar. 7, 2015) "Antitumor effects of pharmacological EZH2 inhibition on malignant peripheral nerve sheath tumor through the miR-30a and KPNB1 pathway" *Mol Cancer*, 14:55, 17 pages.

\* cited by examiner

METHOD FOR TREATING CANCER

RELATED APPLICATIONS

This application is continuation of U.S. application Ser. No. 15/754,684, filed on Feb. 23, 2018, which is a U.S. National Phase application, filed under 35 U.S.C. § 371, of International Application No. PCT/US2016/048401, filed on Aug. 24, 2016, which claims priority to, and the benefit of U.S. Provisional Application No. 62/209,304 filed Aug. 24, 2015, the entire contents of each of which are incorporated herein by reference in their entireties.

BACKGROUND OF THE DISCLOSURE

EZH2, a histone methyltransferase, has been associated with various kinds of cancers. Specifically, mutations and and/or overactivity of EZH2 are found in a range of cancers, such as lymphomas, leukemias and breast cancer. There is an ongoing need for new agents as EZH2 inhibitors for use in anticancer treatment.

SUMMARY OF THE DISCLOSURE

In one aspect, the present disclosure features a method for the treatment or prevention of an INI1-negative tumor. The method comprises administering a therapeutically effective amount of an EZH2 inhibitor to a subject in need thereof.

The method can include one or more of the following features.

In one embodiment, the INI1-negative tumor is rhabdoid tumor of the kidney (RTK).

In one embodiment, the INI1-negative tumor is atypical teratoid/rhabdoid tumor (ATRT).

In one embodiment, the INI1-negative tumor is epithelioid malignant peripheral nerve sheath tumor.

In one embodiment, the INI1-negative tumor is myoepithelial carcinoma.

In one embodiment, the INI1-negative tumor is renal medullary carcinoma.

In one embodiment, the EZH2 inhibitor is administered orally.

In one embodiment, the subject is a human being.

In one embodiment, the subject is younger than 18 years.

In one embodiment, the EZH2 inhibitor is Compound (A), having the following formula

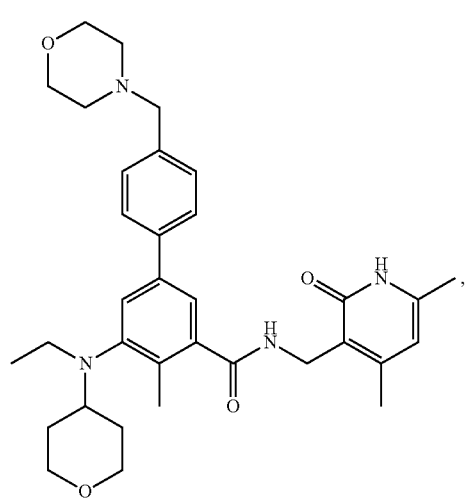

(A)

or a pharmaceutically acceptable salt thereof.

As used herein, the expressions "Compound (A)," "tazemetostat," "EPZ-6438," and "EPZ-6438" all refer to the same Compound (A) and can be used interchangeably.

In one embodiment, the EZH2 inhibitor is administered to the subject at a dose of about 100 mg to about 3200 mg daily.

In one embodiment, the EZH2 inhibitor is administered to the subject at a dose of about 100 mg BID to about 1600 mg BID.

In one embodiment, the EZH2 inhibitor is administered to the subject at a dose of about 100 mg BID, 200 mg BID, 400 mg BID, 800 mg BID, or about 1600 mg BID.

In one embodiment, the EZH2 inhibitor is administered to the subject at a dose of 800 mg BID.

In one embodiment, the EZH2 inhibitor is selected from the group consisting of:

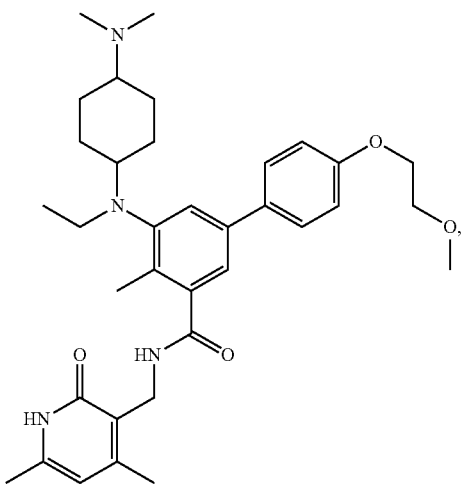

(B)

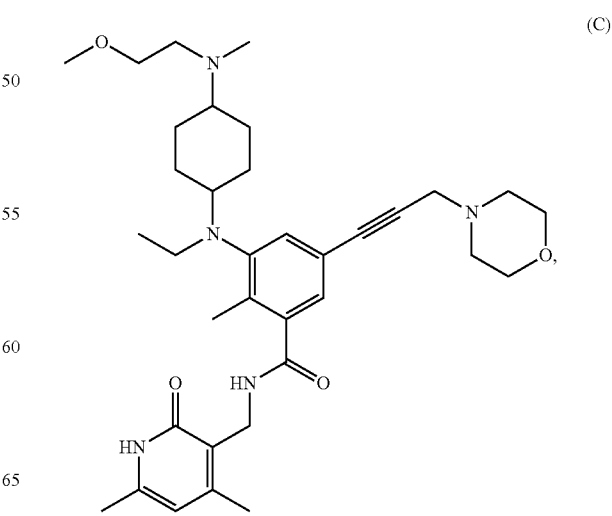

(C)

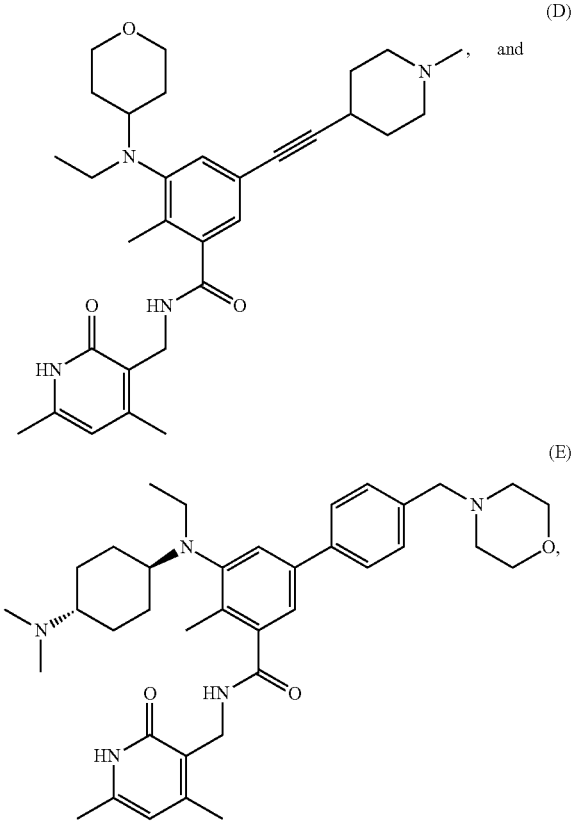

and pharmaceutically acceptable salts thereof.

In one embodiment, the EZH2 inhibitor is:

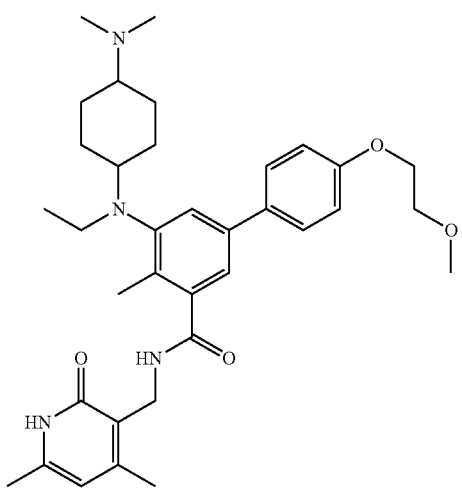

or a pharmaceutically acceptable salt thereof.

Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed disclosure. In the case of conflict, the present specification, including definitions, will control.

In addition, the materials, methods and examples are illustrative only and are not intended to be limiting.

Any of the above aspects and embodiments can be combined with any other aspect or embodiment.

Other features and advantages of the disclosure will be apparent from the following detailed description and claims.

DETAILED DESCRIPTION OF THE DISCLOSURE

Histone methyltransferases (HMTs) play a crucial role in the regulation of gene expression. In particular, HMTs are involved in the regulation of cellular division and of cellular differentiation. HMTs mediate the methylation of histones associated with particular genes. Depending on the amino acid residues that are methylated, the methylation event can either signal a silencing event or an activation event for the associated gene. Examples of a silencing mark include the trimethylation of H3K27; whereas, trimethylation of H3K4 results in a gene activating signal. Many cell cycle check point regulators and tumor suppressor genes exist in a "bivalent" state, wherein these contain both activating histone modifications (e.g. H3K27me3) and suppressing histone modifications (e.g. H3K4me3). Genes in a bivalent state are poised to undergo either activation or suppression depending on external factors. EZH2 regulates bivalent genes involved in B-cell differentiation and maturation, including CDKN1, PRDM1, and IRF4.

EZH2 is a histone methyltransferase that is the catalytic subunit of the PRC2 complex which catalyzes the mono- through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

EZH2 methylation activity plays an important role in the regulation and activation of germinal center B-cells. EZH2 protein levels increase following the activation of B-cells. Following activation, B-cells take residence in the germinal center of lymphoid organs, wherein somatic hypermutation occurs, a process associated with the repression of anti-apoptotic genes and check point regulators. EZH2 methylating events target genes that are involved in B-cell proliferation, differentiation and maturation, including CDKN1A (role in cellular proliferation), PRDM1 (role in B-cell differentiation) and IRF4 (role in B-cell differentiation).

Genetic alterations within the EZH2 gene are associated with altered histone methylation patterns. For example, certain point mutations in EZH2 are associated with altered methylation of H3K4 in DLBCL; furthermore, chromosomal translocation and fusion, SSX:SS18, is associated with altered H3K27 methylation in synovial sarcoma. EZH2 mutations leading to the conversion of amino acid Y641 (equivalent to Y646, catalytic domain), to either F, N, H, S or C results in hypertrimethylation of H3K27 and drives lymphomagenesis. Additional genetic alterations that affect the methylation of H3K27 include EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

EPZ-6438 (Compound (A)) is a small molecule inhibitor of EZH2, the catalytic subunit of the polycomb repressive complex 2 that methylates H3K27. Hypertrimethylation of H3K27 (H3K27Me3) appears tumorigenic in various malignancies, including subsets of Non-Hodgkin Lymphoma (NHL) with mutant EZH2. Inhibition of H3K27Me3 with EPZ-6438 leads to killing of EZH2 mutant lymphoma cells and other EZH2 inhibitors show activity in models of mutant and WT EZH2 NHL. In addition, tumors with loss of INI1, a subunit of the SWI-SNF chromatin remodeling complex, appeared dependent on EZH2. EPZ-6438 was shown to induce apoptosis and differentiation of INI1-deleted malignant rhabdoid tumor (MRT) models in vitro and in MRT xenograft-bearing mice.

This disclosure is based on, at least in part, discovery that Enhancer of Zeste Homolog 2 (EZH2) inhibitors may effectively treat cancer(s), for example cancer(s) that are characterized by aberrant H3-K27 methylation.

An aspect of the present disclosure relates to a method for treating or preventing an INI1-negative tumor. The method comprises administering a therapeutically effective amount of an EZH2 inhibitor to a subject in need thereof. Another aspect relates to a method for treating an INI1-negative tumor. In another aspect, the present disclosure relates to a method for treating an INI1-negative tumor comprising administering a therapeutically effective amount of an EZH2 inhibitor to a subject in need thereof, wherein the INI1-negative tumor is selected from rhabdoid tumor of the kidney (RTK), atypical teratoid/rhabdoid tumor (ATRT), epithelioid malignant peripheral nerve sheath tumor, myoepithelial carcinoma, and renal medullary carcinoma.

Another aspect of the present disclosure relates to a method for treating or preventing a rhabdoid tumor of the kidney (RTK). In another aspect, the present disclosure relates to a method for treating or preventing an atypical teratoid/rhabdoid tumor (ATRT).

Another aspect of the present disclosure relates to a method for treating or preventing an epithelioid malignant peripheral nerve sheath tumor. In another aspect, the present disclosure relates to a method for treating or preventing a myoepithelial carcinoma. Another aspect of the present disclosure relates to a method for treating or preventing a renal medullary carcinoma.

In one embodiment, the EZH2 inhibitor is administered orally.

In one embodiment, the subject is a human being.

In one embodiment, the subject is younger than 18 years. In certain embodiments, in any method described herein, the subject is an adult patient aged 18 years or older.

In certain embodiments, in any method described herein, the subject is a pediatric patient aged 12 months or younger (e.g., between 3 and 12 months old).

In certain embodiments, in any method described herein, the subject is a subject older than 12 months but younger than 18 years old.

In any method described herein, the subject can be a pediatric (non-adult) patient aged 3 months to 18 years.

In any of the above aspects or embodiments, the disclosure also relates to methods for detecting levels of histone methylation, e.g., H3K27 trimethylation, in a skin biopsy. Histone methylation is detected prior to initiation of treatment, while the subject is receiving treatment, and/or after treatment has concluded.

In one embodiment, the compound suitable for the methods disclosed herein is EPZ-6438 (tazemetostat):

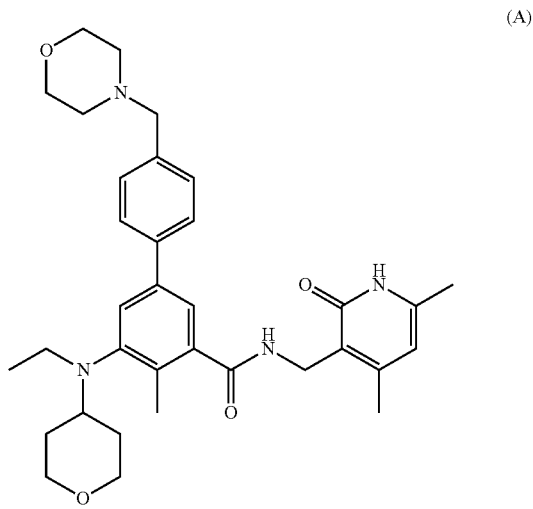 [SMILES: CCN(c1cc(-c2ccc(CN3CCOCC3)cc2)cc(C(=O)NCc2c(C)cc(C)[nH]c2=O)c1C)C1CCOCC1]

(A)

or a pharmaceutically acceptable salt thereof.

EPZ-6438 or a pharmaceutically acceptable salt thereof, as described herein, is potent in targeting both WT and mutant EZH2. EPZ-6438 is orally bioavailable and has high selectivity to EZH2 compared with other histone methyltransferases (i.e. >20,000 fold selectivity by Ki). Importantly, EPZ-6438 has target methyl mark inhibition that results in the killing of genetically defined cancer cells in vitro. Animal models have also shown sustained in vivo efficacy following inhibition of target methyl mark. Clinical trial results described herein also demonstrate the safety and efficacy of EPZ-6438.

In one embodiment, EPZ-6438 or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating a NHL. In one embodiment the dose is 800 mg BID.

In some embodiments, a compound (e.g., EZH2 inhibitor) that can be used in any methods presented here is:

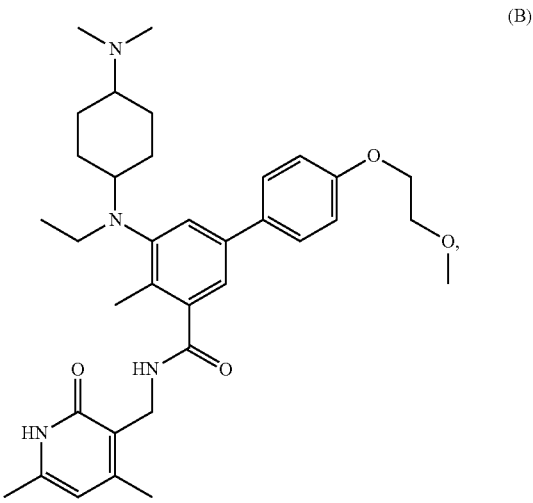

(B)

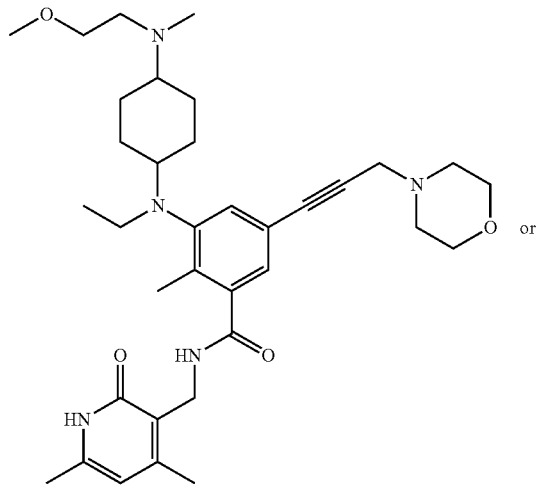
(C)

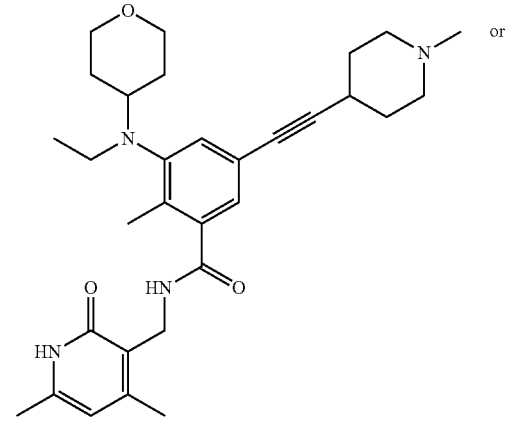
(D)

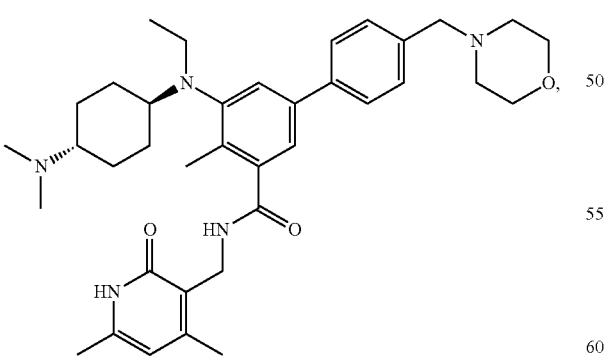
(E)

or stereoisomers thereof or pharmaceutically acceptable salts and solvates thereof.

In certain embodiments, a compound that can be used in any methods presented here is Compound F:

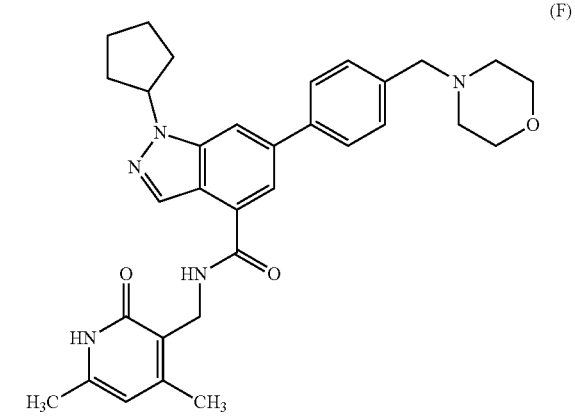 [SMILES: Cc1cc(C)c(CNC(=O)c2cc(-c3ccc(CN4CCOCC4)cc3)cc3c2cnn3C2CCCC2)c(=O)[nH]1]
(F)

or pharmaceutically acceptable salts thereof.

In some embodiments, a compound (e.g., EZH2 inhibitor) that can be used in any methods presented here is GSK-126 having the following formula:

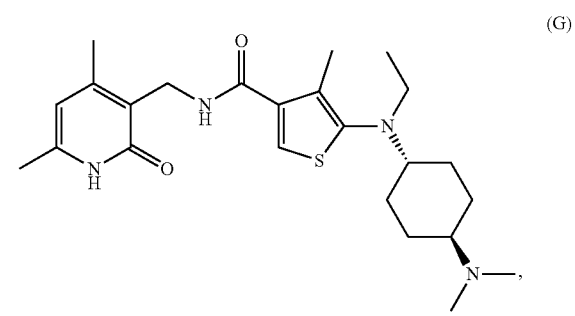

stereoisomers thereof, or pharmaceutically acceptable salts or solvates thereof.

In certain embodiments, a compound that can be used in any methods presented here is Compound G:

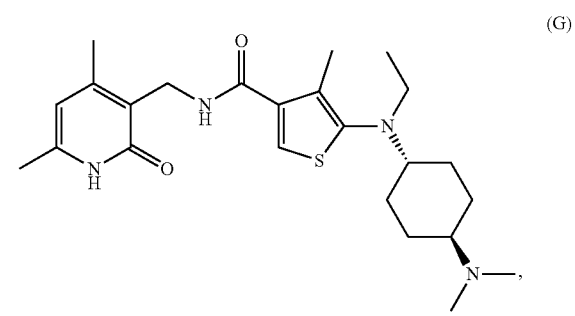
(G)

or stereoisomers thereof or pharmaceutically acceptable salts and solvates thereof.

In certain embodiments, a compound (e.g., EZH2 inhibitor) that can be used in any methods presented here is any of Compounds Ga-Gc:

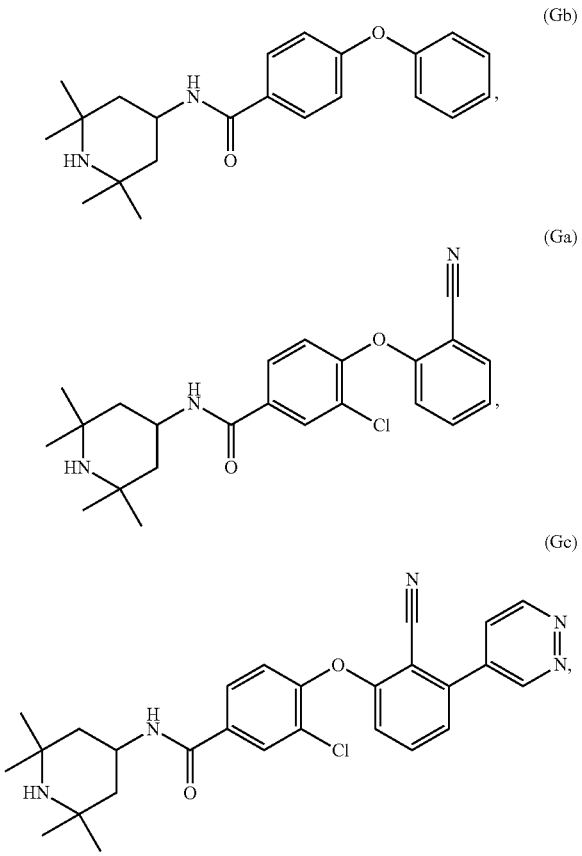

or a stereoisomer, pharmaceutically acceptable salt or solvate thereof.

In certain embodiments, a compound (e.g., EZH2 inhibitor) that can be used in any methods presented here is CPI-1205 or GSK343.

Additional suitable EZH2 inhibitors will be apparent to those skilled in the art. In some embodiments of the strategies, treatment modalities, methods, combinations, and compositions provided herein, the EZH2 inhibitor is an EZH2 inhibitor described in U.S. Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is an EZH2 inhibitor described in PCT/US2014/015706, published as WO 2014/124418, in PCT/US2013/025639, published as WO 2013/120104, and in U.S. Ser. No. 14/839,273, published as US 2015/0368229, the entire contents of each of which are incorporated herein by reference.

In one embodiment, the compound disclosed herein is the compound itself, i.e., the free base or "naked" molecule. In another embodiment, the compound is a salt thereof, e.g., a mono-HCl or tri-HCl salt, mono-HBr or tri-HBr salt of the naked molecule.

Compounds disclosed herein that contain nitrogens can be converted to N-oxides by treatment with an oxidizing agent (e.g., 3-chloroperoxybenzoic acid (mCPBA) and/or hydrogen peroxides) to afford other compounds suitable for any methods disclosed herein. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds disclosed herein can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds disclosed herein may be depicted as different chiral isomers or geometric isomers. It should also be understood that when compounds have chiral isomeric or geometric isomeric forms, all isomeric forms are intended to be included in the scope of the disclosure, and the naming of the compounds does not exclude any isomeric forms.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

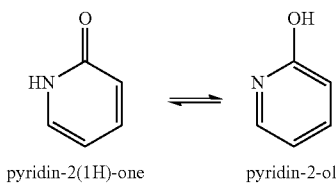 [SMILES: O=c1cccc[nH]1 ; Oc1ccccn1]

pyridin-2(1H)-one      pyridin-2-ol

It is to be understood that the compounds disclosed herein may be depicted as different tautomers. It should also be understood that when compounds have tautomeric forms, all tautomeric forms are intended to be included in the scope of the disclosure, and the naming of the compounds does not exclude any tautomer form.

The compounds disclosed herein include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds disclosed herein, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds disclosed herein are aryl- or heteroaryl-substituted benzene compounds.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In certain aspects, "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition disclosed herein, or a pharmaceutically acceptable salt, solvate, analog or derivative thereof, may be administered in combination with radiation therapy. Radiation therapy can also be administered in combination with a composition disclosed herein and another chemotherapeutic agent described herein as part of a multiple agent therapy.

A "pharmaceutical composition" is a formulation containing a compound in a form suitable for administration to a subject. A compound disclosed herein and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound disclosed herein and one or more other therapeutic agents described herein can be formulated as one pharmaceutical composition.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition disclosed herein is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition disclosed herein can be administered to a subject in many of the well-known methods currently used for chemotherapeutic treatment. For example, for treatment of cancers, a compound disclosed herein may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In any method or formulation (e.g., an oral dosage form) described herein, in one embodiment, said cancer is advanced, refractory or resistant cancer. In any method or formulation (e.g., an oral dosage form) described herein, in one embodiment, said cancer is an INI1-deficient tumor.

INI1 is a critical component of the SWI/SNF regulatory complex, a chromatin remodeler that acts in opposition to EZH2. INI1-negative tumors have altered SWI/SNF function, resulting in aberrant and oncogenic EZH2 activity. This activity can be targeted by small molecule inhibitors of EZH2 such as tazemetostat. INI1-negative tumors are generally aggressive and are poorly served by current treatments. For example, current treatment of MRT, a well-studied INI1-negative tumor, consists of surgery, chemotherapy and radiation therapy, which are associated with limited efficacy and significant treatment-related morbidity.

In any method or formulation (e.g., an oral dosage form) described herein, in one embodiment, the subject is human.

In any method or formulation (e.g., an oral dosage form) described herein when applicable, the cancer is a solid tumor. Examples of the solid tumor described herein include, but are not limited to Colorectal adenocarcinoma, Cholangiocarcinoma, Pancreatic adenocarcinoma, Ewing's sarcoma, Synovial sarcoma, Alveolar sarcoma, Alveolar soft part sarcoma, Prostatic adenocarcinoma, Rhabdoid sarcoma, Malignant Rhabdoid tumor, and Urothelial carcinoma.

In any method or formulation (e.g., an oral dosage form) described herein when applicable, the cancer is a cancer with aberrant H3-K27 methylation.

In any method or formulation (e.g., an oral dosage form) described herein, the compound disclosed herein or a pharmaceutically acceptable salt thereof is administered orally for at least 7, 14, 21, 28, 35, 42, 47, 56, or 64 days. In certain embodiments, the administration is a continuous administration without a drug holiday. For example, the compound disclosed herein or a pharmaceutically acceptable salt thereof is administered orally, for 28 days in a 28-day cycle. In other embodiments, the compound is administered with a drug holiday. For example, a compound disclosed herein or a pharmaceutically acceptable salt thereof is orally administered, e.g., for 21 days of a 28-day cycle with a 7-day drug holiday per cycle.

In any method or formulation (e.g., an oral dosage form) described herein, in certain embodiments, said single dose ranges from about 100 mg to about 1600 mg.

In any method or formulation (e.g., an oral dosage form) described herein, a single dose of a compound disclosed herein or a pharmaceutically acceptable salt thereof is 100, 200, 400, 800 or 1600 mg.

In any method or formulation (e.g., an oral dosage form) described herein, in certain embodiments, said therapeutically effective amount is a single 800 mg dose, wherein said single dose provides a mean AUC(0-12) bioequivalent to a mean AUC(0-12) of from about 7798 ng*hr/ml to about 9441 ng*hr/ml.

In any method or formulation (e.g., an oral dosage form) described herein, in certain embodiments, said therapeutically effective amount is a single 1600 mg dose, wherein said single dose provides a mean AUC(0-12) bioequivalent to a mean AUC(0-12) of from about 15596 ng*hr/ml to about 18882 ng*hr/ml.

In any method or formulation (e.g., an oral dosage form) described herein, in certain embodiments, said therapeutically effective amount is a single 800 mg dose, wherein said single dose provides a mean Cmax bioequivalent to a mean Cmax of from about 1730 ng/ml to about 2063 ng/ml.

In any method or formulation (e.g., an oral dosage form) described herein, in certain embodiments, said therapeutically effective amount is a single 1600 mg dose, wherein said single dose provides a mean Cmax bioequivalent to a mean Cmax of from about 3460 ng/ml to about 4125 ng/ml.

In any method or formulation (e.g., an oral dosage form) described herein, in certain embodiments, said administering comprises administering orally a dosage form to the subject, twice per day or three times per day.

In any method or formulation (e.g., an oral dosage form) described herein, in certain embodiments, said single dose provides a median Tmax of from about 1 hour to about 2 hours.

In any method or formulation (e.g., an oral dosage form) described herein, in certain embodiments, said oral dosage form or formulation comprises an amount of therapeutic agent equivalent to about 25 mg to about 200 mg of EPZ-6438 per unit dose.

In any method or formulation (e.g., an oral dosage form) described herein, in certain embodiments, said oral dosage form or formulation provides an dissolution rate of at least about 90%, or at least about 80%, or at least about 70% in dissolution medium (pH1.2, 37±0.5° C.) within 60 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation provides an dissolution rate of at least about 90%, or at least about 80%, or at least about 70% in dissolution medium (pH1.2, 37±0.5° C.) within 45 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation provides an dissolution rate of at least about 90%, or at least about 80%, or at least about 70% in dissolution medium (pH1.2, 37±0.5° C.) within 30 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation provides an dissolution rate of at least about 80%, or at least about 75%, or at least about 70%, or at least about 60% in dissolution medium (pH4.5 acetate buffer, 37±0.5° C.) within 60 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation comprises sodium starch glycolate or carmellose or a combination thereof as pharmaceutically acceptable carrier or excipient.

Other compounds suitable for the methods of the disclosure are described in U.S. Publication 20120264734, the contents of which are hereby incorporated by reference in their entireties. Further, Compound (A) is suitable for administration as part of a combination therapy with one or more other therapeutic agents or treatment modality, suitable to be administered together, sequentially, or in alternation.

In one embodiment, Compound (A) or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating INI1-negative tumor (e.g., rhabdoid tumor of the kidney (RTK), atypical teratoid/rhabdoid tumor (ATRT), epithelioid malignant peripheral nerve sheath tumor, myoepithelial carcinoma, and renal medullary carcinoma).

The use of the articles "a", "an", and "the" herein are to be construed to cover both the singular and the plural, unless otherwise indicated herein or clearly contradicted by context. For example, the term "a disintegrant" refers to one or more disintegrants included in or suitable for use in the formulation described herein. Similarly, the term "a therapeutic agent" refers to one or more therapeutic agents included in or suitable for use in the formulation described herein. For example, the formulation described herein can include Compound (A) alone as the therapeutic agent or active ingredient or include a mixture of Compound (A) and another compound (e.g., HBr salt of Compound (A) or another anti-cancer drug). The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The concentration of the therapeutic agent in the formulation is expressed as equivalent to a certain amount of Compound (A). As used herein, the term "equivalent" amount or weight percentage refers to the quantity of the drug substance that is adjusted as per potency adjustment factor, a value derived for the assay value obtained from Compound (A). Methods for determining the equivalent amount are well known in the art (see, e.g., http://www.fda.gov/downloads/Drugs/ . . . /Guidances/ucm070246.pdf).

The term "about", "approximately", or "approximate", when used in connection with a numerical value, means that a collection or ranger of values is included. For example, "about x" includes a range of values that are ±10%, +5%, ±2%, ±1%, ±0.5%, ±0.2%, or ±0.1% of X, where X is a numerical value. In addition, "about X" may also include a range of X±0.5, X±0.4, X±0.3, X±0.2, or X±0.1, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present disclosure. Furthermore, so-called metabolite which is produced by degradation of the present compound in vivo is included in the scope of the present disclosure.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "crystal polymorphs", "polymorphs" or "crystalline forms" means crystal structures in which a compound (or a salt or solvate thereof) can crystallize in different crystal packing arrangements, all of which have the same elemental composition. Different crystal forms usually have different XRPD patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the disclosure may be crystalline, semi-crystalline, non-crystalline, amorphous, mesomorphous, etc.

Additionally, the compounds or crystalline forms of the present disclosure, for example, the salts of the compounds or crystalline forms, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof has an INI1-negative tumor.

INI1 is a regulatory complex that opposes the enzymatic function of EZH2. Due to a variety of genetic alterations, INI1 loses its regulatory function. As a result, EZH2 activity is misregulated, causing EZH2 to play a driving, oncogenic role in a set of genetically defined cancers that include rhabdoid tumor of the kidney (RTK), atypical teratoid/rhabdoid tumor (ATRT), epithelioid malignant peripheral nerve sheath tumor, myoepithelial carcinoma, and renal medullary carcinoma.

A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition.

In certain embodiments, in any method described herein, the subject is an adult patient aged 18 years or older.

In certain embodiments, in any method described herein, the subject is a pediatric patient aged 12 months or younger (e.g., between 3 and 12 months old).

In certain embodiments, in any method described herein, the subject is a subject older than 12 months but younger than 18 years old.

In any method described herein, the subject can be a pediatric (non-adult) patient aged 3 months to 18 years.

As used herein, "treating" or "treat" describes the management and care of a patient for the purpose of combating a disease, condition, or disorder and includes the administration of a compound of the present disclosure, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present disclosure, or a pharmaceutically acceptable salt, prodrug, metabolite, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

The methods and uses described herein may include steps of detecting the presence or absence of one or more EZH2 mutations in a sample from a subject in need thereof prior to and/or after the administration of a compound or composition described herein to the subject. By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the disclosure.

The present disclosure also provides pharmaceutical compositions comprising one or more active compounds (e.g., Compound (A) or a salt thereof) in combination with at least one pharmaceutically acceptable excipient or carrier.

In one embodiment, the pharmaceutical composition is in bulk or in unit dosage form. The term "unit dosage form" as used herein refers to physically discrete units suited as unitary dosages for the subject to be treated; each unit containing a predetermined quantity of active compound calculated to produce the desired therapeutic effect in association with the required pharmaceutical carrier. The unit dosage form is any of a variety of forms, including, for example, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

In one embodiment, the unit dosage form is an oral dosage form. In one embodiment, the unit dosage form is a tablet. In one embodiment, the unit dosage form is an oral suspension. In one embodiment, the unit dosage form is an oral suspension and the subject is a pediatric subject.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. For example, a pharmaceutically acceptable excipient used for the formulation of the disclosure can be a diluent or inert carrier, a lubricant, a binder, or a combination thereof. The pharmaceutically acceptable excipient used for the formulation of the disclosure can further include a filler, an anti-microbial agent, an antioxidant, an anti-caking agent, a coating agent, or a mixture thereof.

Examples of pharmaceutically acceptable excipients include, but are not limited to binders, fillers, disintegrants, lubricants, anti-microbial agents, antioxidant, and coating agents.

Exemplary binders include, but are not limited to corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc.), methyl cellulose, Methocel, pre-gelatinized starch (e.g., STARCH 1500® and STARCH 1500 LM®, sold by Colorcon, Ltd.), hydroxypropyl cellulose, hydroxypropyl methyl cellulose, microcrystalline cellulose (FMC Corporation, Marcus Hook, Pa., USA), Emdex, Plasdone, or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof.

Exemplary disintegrants include, but are not limited to: agar-agar, alginic acid, calcium carbonate, microcrystalline cellulose, croscarmellose sodium, crospovidone, polacrilin potassium, sodium starch glycolate (such as Explotab), potato or tapioca starch, other starches, pre-gelatinized starch, clays, other algins, other celluloses, gums (like gellan), low-substituted hydroxypropyl cellulose, ployplasdone, or mixtures thereof.

Exemplary lubricants include, but are not limited to: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Degussa Corp., Plano, Tex. USA), a pyrogenic silicon dioxide (CAB-O-SIL, Cabot Co., Boston, Mass. USA), or mixtures thereof.

Exemplary anti-caking agents include, but are not limited to: calcium silicate, magnesium silicate, silicon dioxide, colloidal silicon dioxide, talc, or mixtures thereof.

Exemplary antimicrobial agents include, but are not limited to: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof.

Exemplary antioxidants include, but are not limited to: ascorbic acid, BHA, BHT, EDTA, or mixture thereof.

Exemplary coating agents include, but are not limited to: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation described herein can also include other excipients and categories thereof including but not limited to Pluronic®, Poloxamers (such as Lutrol® and Poloxamer 188), ascorbic acid, glutathione, protease inhibitors (e.g. soybean trypsin inhibitor, organic acids), pH lowering agents, creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, mannitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In certain embodiments, the formulation of the disclosure is a solid oral dosage form that may optionally be treated with coating systems (e.g. Opadry® fx film coating system) to be coated with for example Opadry® blue (OY-LS-20921), Opadry® white (YS-2-7063), Opadry® white (YS-1-7040), and black ink (S-1-8 106).

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician.

The pharmaceutical compositions of the present disclosure containing active compounds may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed herein are dictated by and directly dependent on the unique characteristics of the active compound and the particular therapeutic effect to be achieved.

In therapeutic applications, the dosages of the EZH2 inhibitor compounds described herein, or the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active Compound (A) and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds in the formulation of the present disclosure are capable of further forming salts. All of these forms are also contemplated within the scope of the claimed disclosure.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in Remington: the Science and Practice of Pharmacy, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound disclosed herein, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound disclosed herein, or a pharmaceutically acceptable salt, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound disclosed herein, or a pharmaceutically acceptable salt or solvate thereof, acts selectively on a cancer or precancerous cell but not on a normal cell. Preferably, a compound disclosed herein, or a pharmaceutically acceptable salt or solvate thereof, acts selectively to modulate one molecular target (e.g., a target protein methyltransferase) but does not significantly modulate another molecular target (e.g., a non-target protein methyltransferase). The disclosure also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition disclosed herein does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound disclosed herein, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound disclosed herein, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition disclosed herein to a cell or a subject in need thereof can result in modulation (i.e., stimulation or inhibition) of an activity of a protein methyltransferase of interest.

Administering a compound disclosed herein, e.g., a composition comprising any compound disclosed herein or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds disclosed herein, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a composition disclosed herein, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition disclosed herein, or a pharmaceutically acceptable salt or solvate thereof, can induce or activate cell death selectively in cancer cells. Administering to a subject in need thereof a compound disclosed herein, or a pharmaceutically acceptable salt or solvate thereof, can induce or activate cell death selectively in cancer cells. Contacting a cell with a composition disclosed herein, or a pharmaceutically acceptable salt or solvate thereof, can induce cell death selectively in one or more cells affected by a cell proliferative disorder. Preferably, administering to a subject in need thereof a composition disclosed herein, or a pharmaceutically acceptable salt or solvate thereof, induces cell death selectively in one or more cells affected by a cell proliferative disorder.

The present disclosure relates to a method of treating or preventing cancer by administering a composition disclosed herein, or a pharmaceutically acceptable salt or solvate thereof, to a subject in need thereof, where administration of the composition disclosed herein, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

Unless specifically stated or obvious from context, as used herein, the term "or" is understood to be inclusive.

Unless otherwise clear from the context, all numerical values provided herein are modified by the term "about."

EXAMPLE

Example 1

INI1 is a critical component of the SWI/SNF regulatory complex, a chromatin remodeler that acts in opposition to EZH2. INI1-negative tumors have altered SWI/SNF function, resulting in aberrant and oncogenic EZH2 activity. This activity can be targeted by small molecule inhibitors of EZH2 such as tazemetostat. INI1-negative tumors are generally aggressive and are poorly served by current treatments. For example, current treatment of MRT, a well-studied INI1-negative tumor, consists of surgery, chemotherapy and radiation therapy, which are associated with limited efficacy and significant treatment-related morbidity.

The adult phase 2 multicenter study will enroll up to 90 patients in three cohorts. The first cohort will be comprised of patients with malignant rhabdoid tumor (MRT), rhabdoid tumor of the kidney (RTK) and atypical teratoid/rhabdoid tumor (ATRT). The second cohort will be comprised of patients with other INI1-negative tumors including epithelioid sarcoma, epithelioid malignant peripheral nerve sheath tumor, extraskeletal myxoid chondrosarcoma, myoepithelial carcinoma, and renal medullary carcinoma. The third cohort will be comprised of patients with synovial sarcoma. Dosing in all three cohorts will be at the recommended phase 2 dose of 800 mg twice per day (BID) with a tablet formulation. The primary endpoint is overall response rate (ORR) for patients with INI1-negative tumors and progression-free survival (PFS) for patients with synovial sarcoma. Secondary endpoints include duration of response, overall survival (OS), PFS for patients with INI1-negative tumors, safety and pharmacokinetics (PK).

The pediatric phase 1 multicenter study will enroll approximately 40 patients in a dose escalation design, followed by dose expansion, with an oral suspension of tazemetostat. The study will enroll subjects with INI1-negative tumors or synovial sarcoma. INI1-negative tumors include MRT, ATRT, RTK, and other INI1-negative tumors as previously described. The primary endpoint of study is safety with the objective of establishing the recommended phase 2 dose in pediatric patients. Secondary endpoints include PK, ORR, duration of response, PFS and OS.

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A method for treating an INI1-negative tumor comprising administering a therapeutically effective amount of an EZH2 inhibitor to a subject in need thereof, wherein the INI1-negative tumor is selected from epithelioid malignant peripheral nerve sheath tumor and myoepithelial carcinoma, wherein the subject is younger than 18 years old and wherein the EZH2 inhibitor is administered to the subject at a dose of about 100 mg to about 3200 mg daily.

2. The method of claim 1, wherein the INI1-negative tumor is epithelioid malignant peripheral nerve sheath tumor.

3. The method of claim 1, wherein the INI1-negative tumor is myoepithelial carcinoma.

4. The method of claim 1, wherein the EZH2 inhibitor is administered orally.

5. The method of claim 1, wherein the subject is a human being.

6. The method of claim 1, wherein the EZH2 inhibitor is Compound (A), having the following formula:

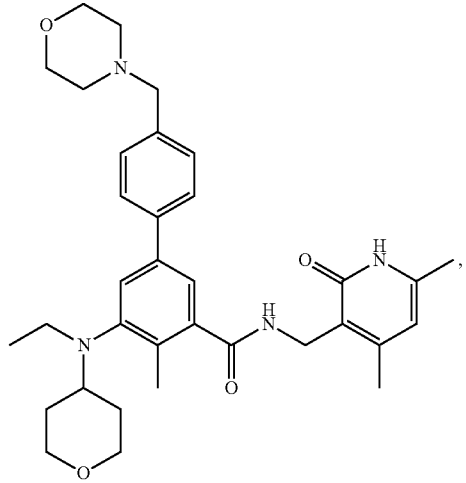

(A)

or a pharmaceutically acceptable salt thereof.

7. The method of claim 1, wherein the EZH2 inhibitor is administered to the subject at a dose of about 100 mg BID to about 1600 mg BID.

8. The method of claim 1, wherein the EZH2 inhibitor is administered to the subject at a dose of about 100 mg BID, 200 mg BID, 400 mg BID, 800 mg BID, or about 1600 mg BID.

9. The method of claim 8, wherein the EZH2 inhibitor is administered to the subject at a dose of 800 mg BID.

10. The method of claim 1, wherein the EZH2 inhibitor is selected from the group consisting of

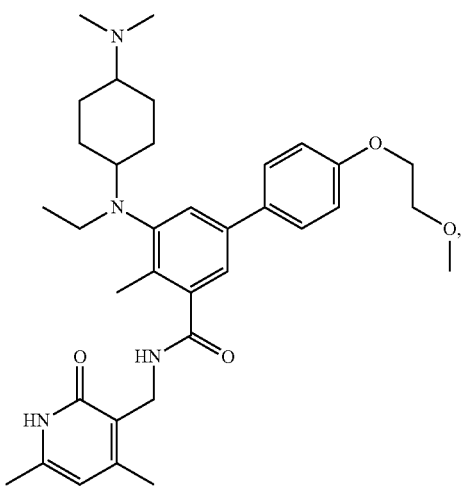
(B)

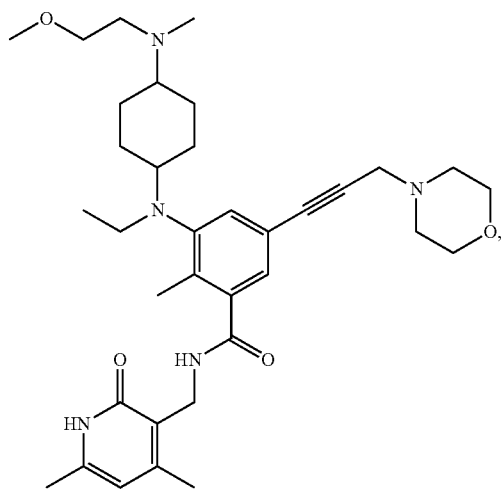
(C)

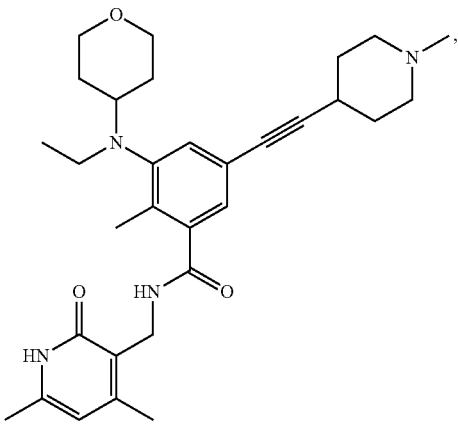
(D)

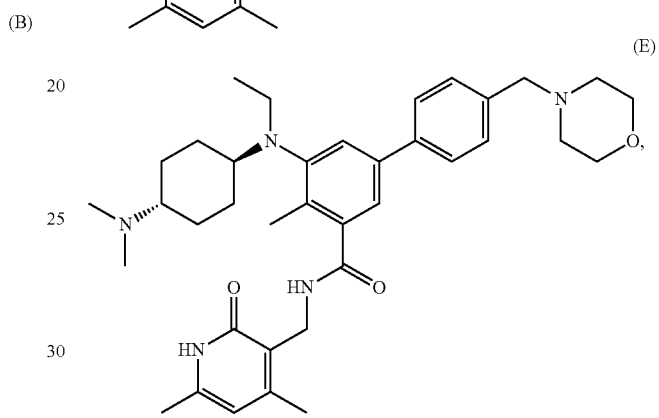
(E)

and pharmaceutically acceptable salts thereof.

11. The method of claim 10, wherein the EZH2 inhibitor is:

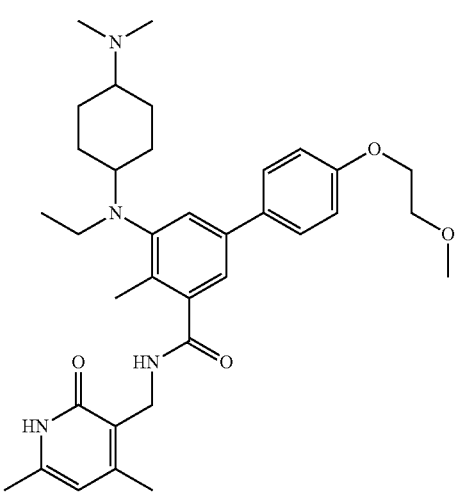
(B)

or a pharmaceutically acceptable salt thereof.

* * * * *